(12) United States Patent
Smith et al.

(10) Patent No.: US 6,819,949 B2
(45) Date of Patent: Nov. 16, 2004

(54) METHOD AND APPARATUS FOR MEASURING BLOOD OXYGEN SATURATION IN A RETINAL VESSEL BY SEPARATELY DETECTING SINGLE PASS OPTICAL SIGNALS

(75) Inventors: Matthew H. Smith, Madison, AL (US); Arthur Lompado, Huntsville, AL (US); Kurt R. Denninghoff, Birmingham, AL (US); Lloyd W. Hillman, Huntsville, AL (US)

(73) Assignee: University of Alabama in Huntsville, Huntsville, AL (US)

( * ) Notice: Subject to any disclaimer, the term of this patent is extended or adjusted under 35 U.S.C. 154(b) by 36 days.

(21) Appl. No.: 10/134,360

(22) Filed: Apr. 29, 2002

(65) Prior Publication Data

US 2002/0188203 A1 Dec. 12, 2002

Related U.S. Application Data (60) Provisional application No. 60/287,623, filed on Apr. 30, 2001.

(51) Int. Cl.$^7$ ................................................ A61B 5/00
(52) U.S. Cl. .................................... 600/318; 600/323
(58) Field of Search ................................ 600/322–323, 600/318–320

(56) References Cited

U.S. PATENT DOCUMENTS

| | | | |
|---|---|---|---|
| 5,119,814 A | 6/1992 | Minnich | |
| 5,308,919 A | 5/1994 | Minnich | |
| 5,776,060 A | 7/1998 | Smith et al. | |
| 5,935,076 A | 8/1999 | Smith et al. | |
| 6,236,877 B1 * | 5/2001 | Elsner et al. | 600/407 |
| 6,244,712 B1 | 6/2001 | Smith et al. | |

OTHER PUBLICATIONS

D. Schweitzer, B. Kalve, M. Hammer, L. Leistritz, *Oxygen Saturation Is Not Measurable Sufficient Exactly By Laser Scanner Technique*, Invest. Ophthalmol. Vis. Sci. (Suppl.), 1997, 1 page, vol. 38, S101.

Dietrich Schweitzer, Martin Hammer, Janine Kraft, Eike Thamm, Ekkehart Konigsdorffer, Jurgen Strobel, *In Vivo Measurement Of The Oxygen Saturation Of Retinal Vessels I n Healthy Volunteers*, IEEE Transactions On Biomedical Engineering, Dec. 1999, pps. 1454–1465, vol. 46, No. 12.

A.E. Elsner, L. Moraes, E. Beausencourt, A. Remky, S.A. Burns, J.J. Weiter, J.P. Walker, G.L. Wing, P.A. Raskauskas, L.M. Kelley, *Scanning Laser Reflectometry Of Retinal And Subretinal Tissues*, Optics Express, Jun. 19, 2000, pps. 243–250, vol. 6, No. 13.

\* cited by examiner

*Primary Examiner*—Mary Beth Jones
*Assistant Examiner*—Matthew Kremer
(74) *Attorney, Agent, or Firm*—Alston & Bird LLP (57) ABSTRACT

A method and apparatus are provided for accurately measuring the blood oxygen saturation with a retinal vessel. The apparatus includes an optical source for illuminating the retinal vessel with optical signals. The apparatus also includes a filter, such as an aperture, disposed within the path of the optical signals returning from the eye. The filter preferentially passes single pass optical signals that have diffused through the retinal layer and/or the choroidal layer of the eye while traversing the retinal vessel only once, while blocking or otherwise redirecting the other optical signals. The apparatus also includes a detector for separately detecting at least the single pass optical signals and, in some instances, the other optical signals as well. The apparatus can also include a processing element for determining the blood oxygen saturation in the retinal vessel based upon the optical signals that have been detected.

18 Claims, 5 Drawing Sheets

METHOD AND APPARATUS FOR MEASURING BLOOD OXYGEN SATURATION IN A RETINAL VESSEL BY SEPARATELY DETECTING SINGLE PASS OPTICAL SIGNALS

CROSS-REFERENCE TO RELATED APPLICATIONS

The present application claims priority from U.S. Provisional Application No. 60/287,623 filed Apr. 30, 2001 by Matthew H. Smith, et al., the contents of which are incorporated herein in their entirety.

FEDERALLY SPONSORED RESEARCH OR DEVELOPMENT

The United States Government may have rights in the inventions set forth herein as provided by the terms of Contract No. DAMD17-98-1-8007 awarded by the U.S. Medical Army Research and Materials Command and Contract No. NOOO14-99-1-0226 awarded by the Office of Naval Research.

FIELD OF THE INVENTION

The present invention relates generally to methods and apparatus for measuring blood oxygen saturation in a retinal vessel and, more particularly, to methods and apparatus for measuring blood oxygen saturation in a retinal vessel based upon the separate detection of optical signals that traverse the retinal vessel a single time, thereby obtaining well-calibrated measurements of the blood oxygen saturation of the blood within the retinal vessel. In this regard, the method and apparatus of the present invention advantageously separate optical signals that pass through the retinal vessel multiple times, optical signals that reflect from the retinal vessel and optical signals that are backscattered by red blood cells within the retinal vessel from optical signals that traverse the retinal vessel a single time such that the optical signals that traverse the retinal vessel a single time can be separately detected and processed, with the other optical signals being either discarded or similarly separately detected and processed.

BACKGROUND OF THE INVENTION

A variety of spectroscopic oximetry techniques have been developed to monitor the blood oxygen saturation and blood oxygen content in retinal vessels. By monitoring the blood oxygen saturation, the arteriovenous oxygen difference can be determined as described by U.S. Pat. No. 5,308,919 to Thomas E. Minnich, U.S. Pat. No. 5,776,060 to Matthew H. Smith, et al., and U.S. Pat. No. 5,935,076 to Matthew H. Smith, et al. Based upon the arteriovenous oxygen difference, the cardiac output of a subject can be determined in order to assist in post-operative monitoring and the management of critically ill patients. By monitoring the blood oxygen saturation, the loss of blood can be detected, and the rate and quantity of blood loss over time can be estimated as described by U.S. Pat. No. 5,119,814 to Thomas E. Minnich.

In addition to the variety of invasive techniques that require blood to be drawn, oftentimes repeatedly, from a patient, a number of non-invasive spectroscopic oximetry techniques have been developed to measure the blood oxygen saturation of a patient without requiring blood to be drawn from the patient. For example, a number of noninvasive spectroscopic oximetry techniques have been developed which measure the blood oxygen saturation of a patient based upon the transmittance of the blood within a retinal vessel, such as a retinal vein or a retinal artery. For example, U.S. Pat. Nos. 5,776,060 and 5,935,076 describe techniques for measuring the oxygen saturation of blood within a retinal vessel by illuminating the retinal vessel with light having a combination of wavelengths and then measuring the transmittance of the blood within the retinal vessel in response to the illumination at each of the selected wavelengths. Based upon the respective transmittance of the blood within the retinal vessel that is measured at each of the selected wavelengths, the oxygen saturation of the blood within the retinal vessel can be determined. The contents of U.S. Pat. Nos. 5,776,060 and 5,935,076 are hereby incorporated by reference in their entirety.

As will be apparent, the light with which a retinal vessel is illuminated can be reflected and transmitted in a variety of different manners. For example, some of the light will be immediately reflected by the retinal vessel, while other portions of the light will be backscattered by the red blood cells within the retinal vessel. Other portions of the light, termed "double pass light", will pass through the retinal vessel, be reflected from the retinal and/or choroidal layers and again pass through the retinal vessel, thereby traversing the retinal vessel twice. Further, some portion of the light, termed "single pass light", will pass through the retinal vessel, diffuse laterally through the retinal and/or choroidal layers and then exit the pupil without again traversing the retinal vessel.

Regardless of the particular paths traveled by the optical signals, the optical signals that return from the eye are collected by a detector and an associated processing element, such as a microprocessor, a personal computer or the like, can determine the blood oxygen saturation within the retinal vessel based upon the light that is returned. In order to determine the blood oxygen saturation, techniques have been developed to account for light that has been reflected and/or transmitted in each of the various manners described above. As a result of the variety of different ways in which light can be reflected and/or transmitted, however, the equations that must be solved to determine the blood oxygen saturation within the retinal vessel are quite complicated and may reduce the accuracy with which the blood oxygen saturation can be determined.

In this regard, the single pass light contains information relevant to determining the oxygen saturation of the blood in the retinal vessel. However, the light that is returned from the eye and is detected includes not only the single pass light but also light that has propagated along other paths, such as light that is reflected from the retinal vessel, light that has been back scattered by the red blood cells within a retinal vessel and double pass light. While the light that has propagated along these other paths is helpful in creating a visual image of the retinal vessel, the light that has propagated along these other paths is generally less valuable for purposes of determining the oxygen saturation of the blood within the retinal vessel than the single pass light.

While the separation of the single pass light from the other components of the returning light would simplify the equations that must be solved to determine the blood oxygen saturation and improve the accuracy with which the blood oxygen saturation can be determined, it has heretofore been difficult to separate the single pass light that contains the information of merit from the light that has propagated along other paths. Thus, while advantageous non-invasive spectroscopic oximetry techniques have been developed, it would be desirable to improve these techniques in order to more accurately determine the oxygen saturation of the blood within a retinal vessel.

SUMMARY OF THE INVENTION

A method and apparatus are provided for more accurately measuring the blood oxygen saturation with a retinal vessel. In this regard, the method and apparatus separate the single pass optical signals that have only traversed the retinal vessel once from the other optical signals. By separately detecting and analyzing the single pass optical signals, the method and apparatus can measure the blood oxygen saturation within the retinal vessel in a more straightforward manner utilizing simplified equations, thereby permitting a more accurate measurement of the blood oxygen saturation.

According to one aspect of the present invention, the apparatus generally includes an optical source for illuminating the retinal vessel with optical signals. The apparatus also includes a filter disposed within the path of the optical signals returning from the eye. The filter is capable of separating the single pass optical signals from the other optical signals that return from the eye. The filter may be disposed at a focal point of the optical signals returning from the eye to block or otherwise redirect the other optical signals, while permitting the single pass optical signals to pass. In one embodiment, the filter is an aperture that has a central stop and a transmissive portion at least partially surrounding the stop to only permit some optical signals to pass. As such, the aperture preferentially passes single pass optical signals that have diffused through the retinal layer and/or the choroidal layer of the eye while traversing the retinal vessel only once. The aperture can have a variety of designs. For example, the aperture can be an annulus, an anti-pinhole, a slit-annulus or an anti-slit. Regardless of the configuration, the central stop of one embodiment of the aperture is at least partially reflective to selectively redirect the other optical signals.

The apparatus also includes a detector for detecting at least the single pass optical signals that have been separated from the other optical signals by the filter. In one embodiment, the detector may also separately detect the other optical signals that have been separated from the single pass optical signals by the filter. The apparatus may further include a processing element for determining the blood oxygen saturation within the retinal vessel based upon at least the single pass optical signals. In the embodiment in which the detector also separately detects the other optical signals, the processing element can determine the blood oxygen saturation within the retinal vessel based upon the separate contributions of the single pass optical signals and the other optical signals. In either instance, the processing element can determine the blood oxygen saturation within the retinal vessel based upon a simplified set of equations since the single pass optical signals have been separated from the other optical signals, thereby permitting increased accuracy in the determination of the blood oxygen saturation within the retinal vessel.

According to another aspect of the present invention, a method for separately detecting single pass optical signals is provided. According to this method, a retinal vessel within the eye is illuminated with optical signals. The single pass optical signals that return from the eye are separated from the other optical signals and detected. In one embodiment, the other optical signals are redirected and may also be detected, albeit separately from the single pass optical signals. In order to separate the single pass optical signals from the other optical signals, the optical signals returning from the eye that are focused upon a stop, i.e., the other optical signals, may be blocked, while passing the optical signals that are offset from the stop, i.e., the single pass optical signals. Regardless of the manner in which the single pass optical signals are separated from the other optical signals, the blood oxygen saturation within the retinal vessel may be determined based upon the single pass optical signals and, in some embodiments, the other optical signals that have been detected.

According to the present invention, the single pass optical signals are separated from the other optical signals, such as the optical signals that have reflected from the retinal vessel and that have been backscattered by the red blood cells within the retinal vessel as well as the double pass optical signals. By separating the single pass optical signals from the other optical signals, the method and apparatus need not attempt to solve the complex equations that are otherwise required to determine the blood oxygen saturation in instances in which all of the returning optical signals are detected as a whole. Instead, the method and apparatus of the present invention can utilize equations that define the blood oxygen saturation based upon the detected optical signals that are greatly simplified and the blood oxygen saturation values that are determined according to the method and apparatus of the present invention may therefore have increased accuracy relative to conventional techniques.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE PRESENT INVENTION

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Figure 1:
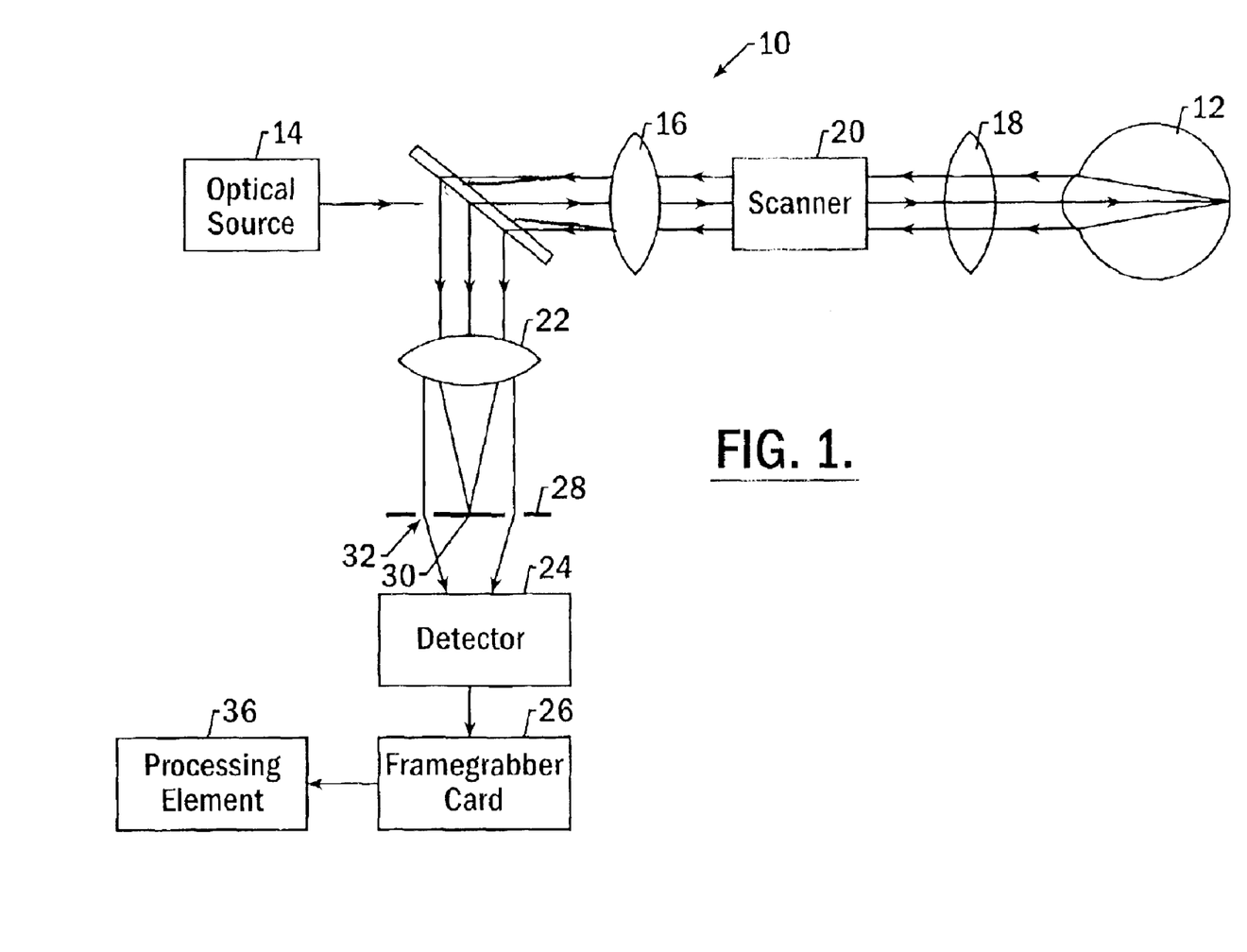
FIG. 1 is a block diagram of an apparatus for measuring the blood oxygen saturation in a retinal vessel according to one embodiment of the present invention.

Referring now to FIG. 1, an apparatus 10 for separately detecting single pass optical signals and for correspondingly measuring the transmittance of the retinal vessel and, in turn, calculating the blood oxygen saturation in the retinal vessel within the eye 12 based upon the measured transmittance according to one embodiment of the present invention is depicted. The apparatus includes an optical source 14 for illuminating the retinal vessels with optical signals. Typically, the optical source comprises a plurality of lasers, such as a plurality of diode lasers, for emitting laser signals having different respective wavelengths. While the apparatus can include any number of lasers, such as three lasers or five lasers, the apparatus of one advantageous embodiment includes four lasers for emitting laser signals having four different wavelengths as described by U.S. Pat. No. 6,244,712 by Matthew H. Smith, et al. which issued on Jun. 12, 2001, the contents of which are incorporated herein by reference. In this regard, the plurality of lasers can be selected to have any combination of wavelengths. In order to monitor the oxygen saturation or oxygen content of the blood in retinal vessels, however, the apparatus of this embodiment preferably includes four lasers that emit optical signals having wavelengths of 488 nm, 635 nm, 670 nm and 830 nm. However, the apparatus can include other types of optical sources, such as white light sources or optical sources that provide spectrally filtered light, if so desired.

In the embodiment in which the optical source 14 comprises a plurality of lasers, the apparatus 10 also typically includes one or more beam combiners (not shown), such as one or more dichroic beam combiners, for combining the laser signals emitted by the plurality of lasers to form a composite beam having each of the different respective wavelengths. The apparatus can also include a polarizer (not shown) for insuring that the laser signals are appropriately polarized.

Regardless of the combination and/or polarization of the optical signals, the optical signals are directed to illuminate the posterior portion of a subject's eye 12. In order to measure the blood oxygen content of the retinal vessels, the apparatus 10 illuminates the retina including the retinal vessels disposed along the rear surface of the eye. While the optical signals can be directed in a number of different fashions, the apparatus can include one or more lenses, including a focusing lens 16 and/or an imaging lens 18.

The apparatus 10 is generally designed to repeatedly scan the optical signals across the posterior portion of the eye 12. As such, the apparatus also includes a scanner 20, such as a 2-axis scanner. Although the optical signals can be scanned in a variety of different fashions, the scanner typically raster scans the optical signals in a predetermined pattern across the posterior portion of the eye, thereby defining an image having a plurality of scanned lines.

The optical signals impinging upon the retinal vessels are reflected and transmitted in a variety of different manners. In this regard, some of the optical signals are reflected by the retinal vessel, while other optical signals are backscattered by the red blood cells within the retinal vessel. Other optical signals, i.e., double pass signals, pass through the retinal vessel, are reflected by the retinal and/or choroidal layers and pass through the retinal vessel for a second time. Still other optical signals, i.e., single pass signals, pass completely through the retinal vessel, diffuse laterally through the retinal and/or choroidal layers and exit the pupil without again passing through the retinal vessel. Optical signals that have been reflected and transmitted in each of these manners are then returned from the eye 12 and are focused toward a focal point, such as by means of a focusing lens 22, and are collected by a detector 24, such as a photodetector and, more particularly, an avalanche photodiode or a photomultiplier tube. The detector typically measures the intensity of the optical signals and generates a time-varying signal based upon the detected intensity. As a result of the scanning of the optical signals in a predetermined pattern of scan lines across the posterior portion of the eye, the output of the detector will be time-varying. The detector then provides the time-varying output to means, such as a frame grabber card 26, for performing a time-to-space conversion so as to construct a data frame or image from the signals provided by the detector.

According to the present invention, a filter 28 is disposed in the return path of the optical signals in order to block or otherwise redirect some of the optical signals and thereby prevent those optical signals from reaching the detector 24. In the embodiment illustrated in FIG. 1, the apparatus 10 includes a filter disposed between the focusing lens 22 and the detector. Typically, the filter is confocal to the reflecting surface, i.e., the ocular fundus, of the retina such that the filter is placed at the image of the retinal area being illuminated by the optical source 14.

The filter 28 separates the single pass optical signals from the other optical signals that return from the eye 12, i.e., the optical signals are reflected by the retinal vessel, the optical signals that are backscattered by the red blood cells within the retinal vessel and double pass signals. In one embodiment, the filter separates the single pass optical signals by preferentially permitting the single pass optical signals to pass therethrough, while blocking or otherwise redirecting the other optical signals.

In one embodiment, the filter 28 is formed by an aperture that includes a central stop 30 and a transmissive portion 32 at least partially surrounding the stop. As described above, the aperture is advantageously confocal to the reflecting surface of the retina such that the center of the aperture, i.e., the central stop, is placed at the image of the retinal area being illuminated by the optical source 14. As such, optical signals that are focused by the focusing lens 22 to be incident upon the stop are blocked or otherwise redirected by the stop while optical signals that are offset from the stop are permitted to pass through the transmissive portion of the aperture. In this regard, the majority of the optical signals that are reflected by the retinal vessel and that are backscattered by the red blood cells within the retinal vessel as well as the double pass signals are focused by the focusing lens to be incident upon the stop. As such, the stop of the aperture blocks or otherwise redirects these components of the optical signals. However, the single pass optical signals that have passed through the retinal vessel, diffused laterally through the retinal and/or choroidal layers of the eye 12 and then exited the pupil without again passing through the retinal vessel are not focused to upon the stop by the focusing lens. Instead, these single pass optical signals are offset laterally from the focal point so as to pass through the transmissive portion of the aperture.

Figure 2A:
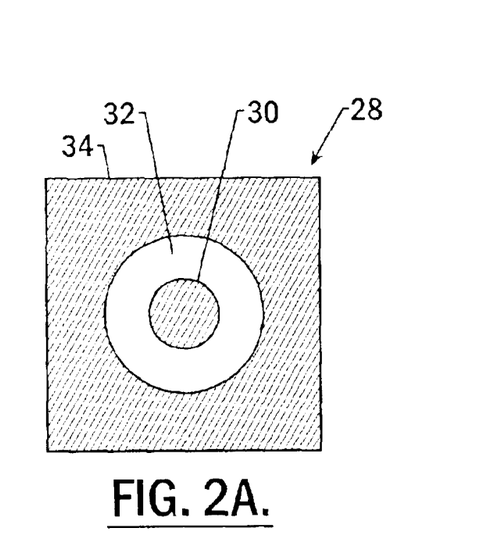
FIGS. 2A–2D are apertures of various embodiments of the present invention.
Figure 2B:
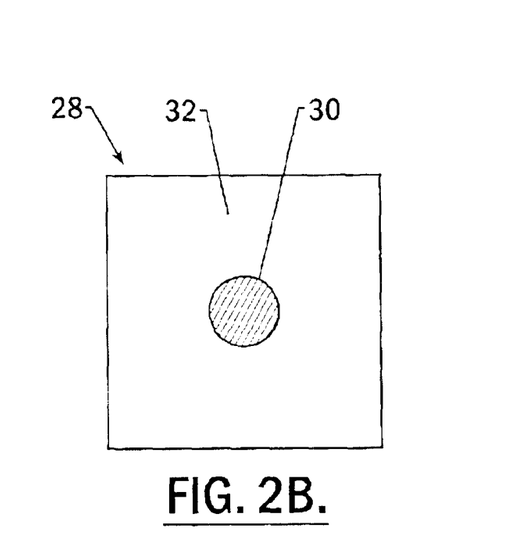
Figure 2C:
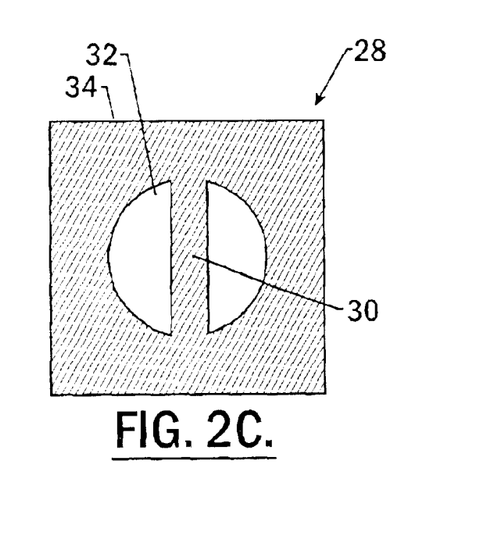
Figure 2D:
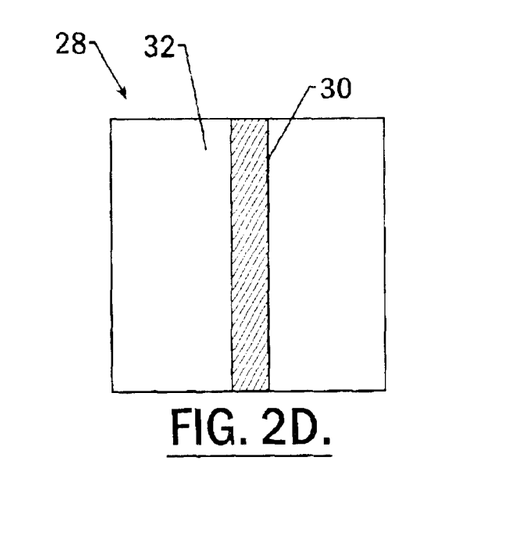

The aperture can have several different configurations, a few of which are illustrated in FIGS. 2A–2D. In each of these embodiments, the central stop 30 is represented by the centrally located dark region which is opaque to the optical signals, while the transmissive portion 32 is indicated by the light regions that are transparent to the optical signals. Referring to FIG. 2A, for example, the aperture of one embodiment can include a centrally located stop surrounded by an annular transmissive portion which, in turn, is surrounded by an opaque border 34, thereby resulting in an annulus configuration. Alternatively, an anti-pinhole configuration is depicted in FIG. 2B which is similar to the annulus design in that the stop is centrally located and is surrounded by the transmissive portion. However, the anti-pinhole design does not include an opaque frame in the same manner as the annulus configuration. In the embodiment of FIG. 2C, a slit-annulus configuration is depicted. In this configuration, the stop is a linear opaque strip and the transmissive portion is comprised of a pair of arcuate segments disposed on opposite sides of the stop. While the transmissive portions of the slit-annulus configuration are depicted to be arcuate, the transmissive portions can have other shapes, if so desired. In the slit-annulus configuration depicted in FIG. 2C, the aperture also includes an opaque border surrounding the stop and the transmissive portion. However, the aperture need not include the opaque border. For example, the anti-slit configuration of FIG. 2D also includes a stop formed of a linear opaque strip and the transmissive portion is comprised of transparent regions on opposite sides of the linear stop.

With respect to the annulus and anti-pinhole configurations of FIGS. 2A and 2B, the aperture is positioned in the return path of the optical signals and, more particularly, within the focal plane of the focusing lens 22 with the center of the stop 30 being positioned at the focal point along the optical axis defined by the focusing lens. With respect to the slit-annulus and anti-slit configurations of FIGS. 2C and 2D, the aperture is again positioned within the return path of the optical signals and, more particularly, within the focal plane of the focusing lens with a central portion of the stop being located at the focal point along the optical axis defined by the focusing lens. However, the slit-annulus and anti-slit configurations are also preferably disposed such that the linear strip that forms the stop is aligned with the retinal vessel that is currently being examined.

By separating the optical signals that have reflected from the retinal vessel and been backscattered by the red blood cells within the retinal vessel as well as the double pass signals, from the single pass optical signals, the determination of the blood oxygen saturation is simplified and the accuracy with which this determination is made is increased as described below. For example, in embodiments in which the other optical signals that have been separated from the single pass optical signals are blocked, a high percentage, if not all, of the optical signals that arrive at the detector 24 are the single pass optical signals that contain information relevant to the determination of the oxygen saturation of the blood within the retinal vessel.

Figure 3:
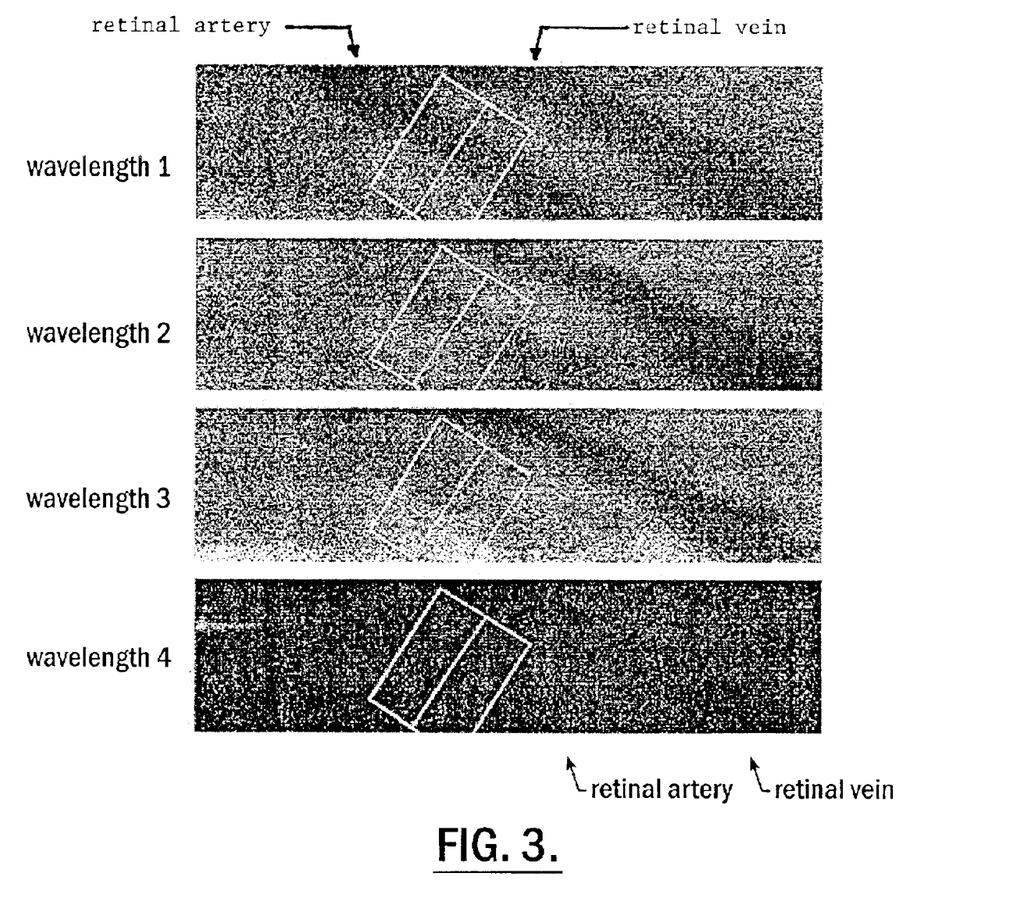
FIG. 3 presents images of a retinal vein and a retinal artery taken at four different wavelengths according to the method and apparatus of one embodiment of the present invention.

The apparatus 10 also generally includes a processing element 36, such as a processor, a personal computer or other computer device for performing the functions described hereinbelow. The processing element receives the data frames provided by the detector 24 and the associated frame grabber card 26 of the illustrated embodiment. The processing element can provide for the display of the images represented by the data frames. In this regard, FIG. 3 depicts the images of a retinal vein and a retinal artery that are reconstructed from single pass optical signals having four different wavelengths. Since a substantial amount of the other optical signals have been blocked by the filter 28 of this embodiment, the images tend to have a relatively low contrast. However, the processing element can readily determine the blood oxygen saturation based upon data represented by these images in more accurate fashion than provided by conventional techniques. In this regard, the measured transmittance of a retinal vessel for optical signals having a wavelength $\lambda$ is $T_v(\lambda)$ which can be approximated as follows:

$$T_v(\lambda) = a(\lambda) exp[-\chi \epsilon(\lambda) cd] \qquad (1)$$

wherein $$\epsilon(\lambda) = s\epsilon_{HbO_2}(\lambda) + (1-s)\epsilon_{Hb}(\lambda) \qquad (2)$$

and wherein $a(\lambda)$ is the component of the incident optical signals that underwent single-pass transmission, i.e., single pass optical signals, s is oxygen saturation, c is hemoglobin concentration, d is path length, i.e., the vessel diameter, $\epsilon_{Hb}(\lambda)$ is the absorption coefficient of deoxyhemoglobin, and $\epsilon_{HbO_2}(\lambda)$ is the absorption coefficient of oxyhemoglobin. In addition, $\chi$ is a factor that defines the type of optical signals that are detected with $\chi=1$ representing that all of the optical signals are single pass optical signals, $\chi=2$ representing that all of the optical signals are double pass optical signals and $1<\chi<2$ representing that the optical signals are a combination of both single and double pass optical signals.

The general representation of $T_v(\lambda)$ and $\epsilon(\lambda)$ set forth above in equations (1) and (2), respectively, can be rewritten to more specifically account for the different effects of absorption and scattering upon the optical signals as follows:

$$T_v(\lambda) = a(\lambda) exp[-\chi \epsilon_{abs}(\lambda) cd] \qquad (3)$$

wherein $$a(\lambda) = exp[\chi \epsilon_{scat}(\lambda) cd] \qquad (4)$$

and wherein $$\epsilon_{abs}(\lambda) = s\epsilon_{abs\ HbO_2}(\lambda) + (1-s)\epsilon_{abs\ Hb}(\lambda) \qquad (5)$$

$$\epsilon_{scat}(\lambda) = s\epsilon_{scat\ HbO_2}(\lambda) + (1-s)\epsilon_{scat\ Hb}(\lambda) \qquad (6)$$

In the foregoing equations, $\epsilon_{abs\ Hb}(\lambda)$ now represents the absorption coefficient of deoxyhemoglobin, and $\epsilon_{abs\ HbO_2}(\lambda)$ now represents the absorption coefficient of oxyhemoglobin. Similarly, $\epsilon_{scat\ Hb}(\lambda)$ is the scattering coefficient of deoxyhemoglobin, and $\epsilon_{scat\ HbO_2}(\lambda)$ is the scattering coefficient of oxyhemoglobin. Moreover, it will be noted from the foregoing equations that $a(\lambda)$ is dependent upon the scattering properties of the tissue, among other things.

The processing element 36 can therefore determine the oxygen saturation of blood within a retinal vessel by applying the foregoing equations, namely, equations (3)–(6) to the data collected by the detector 24 at different wavelengths. In this regard, the $a(\lambda)$ can be determined based upon the ratio of the return signals at a respective point to the intensity of the incident optical signals at that point. By utilizing the data collected at at least two wavelengths, the equations can be solved for s and cd since the terms $\epsilon_{abs\ Hb}(\lambda)$ and $\epsilon_{abs\ HbO_2}(\lambda)$ are well known functions of wavelength. In addition, $\epsilon_{scat\ Hb}(\lambda)$ and $\epsilon_{scat\ HbO_2}(\lambda)$ for a retinal vessel can be estimated based upon values of $\epsilon_{scat\ Hb}(\lambda)$ and $\epsilon_{scat\ HbO_2}(\lambda)$ that have been previously defined for other optical elements as will be apparent to those skilled in the art. Alternatively, $\epsilon_{scat\ Hb}(\lambda)$ and $\epsilon_{scat\ HbO_2}(\lambda)$ can determined by illuminating the retinal vessel with light having other wavelengths and then solving the above equations, not only for s and cd, but also for $\epsilon_{scat\ Hb}(\lambda)$ and $\epsilon_{scat\ HbO_2}(\lambda)$ as will also be apparent to those skilled in the art.

As a result of filtering or blocking the other optical signals that have been separated from the single pass optical signals, such as the optical signals that reflect from the retinal vessel and that are backscattered by the red blood cells of the retinal vessel as well as the double pass signals, $\chi$ will equal 1 and the resulting equations are greatly simplified relative to the comparable equations utilized by other techniques that account for all of the various paths of light. As such, the apparatus and method of the present invention can determine the blood oxygen saturation in a more computationally efficient and accurate fashion than provided by conventional techniques.

Figure 4:
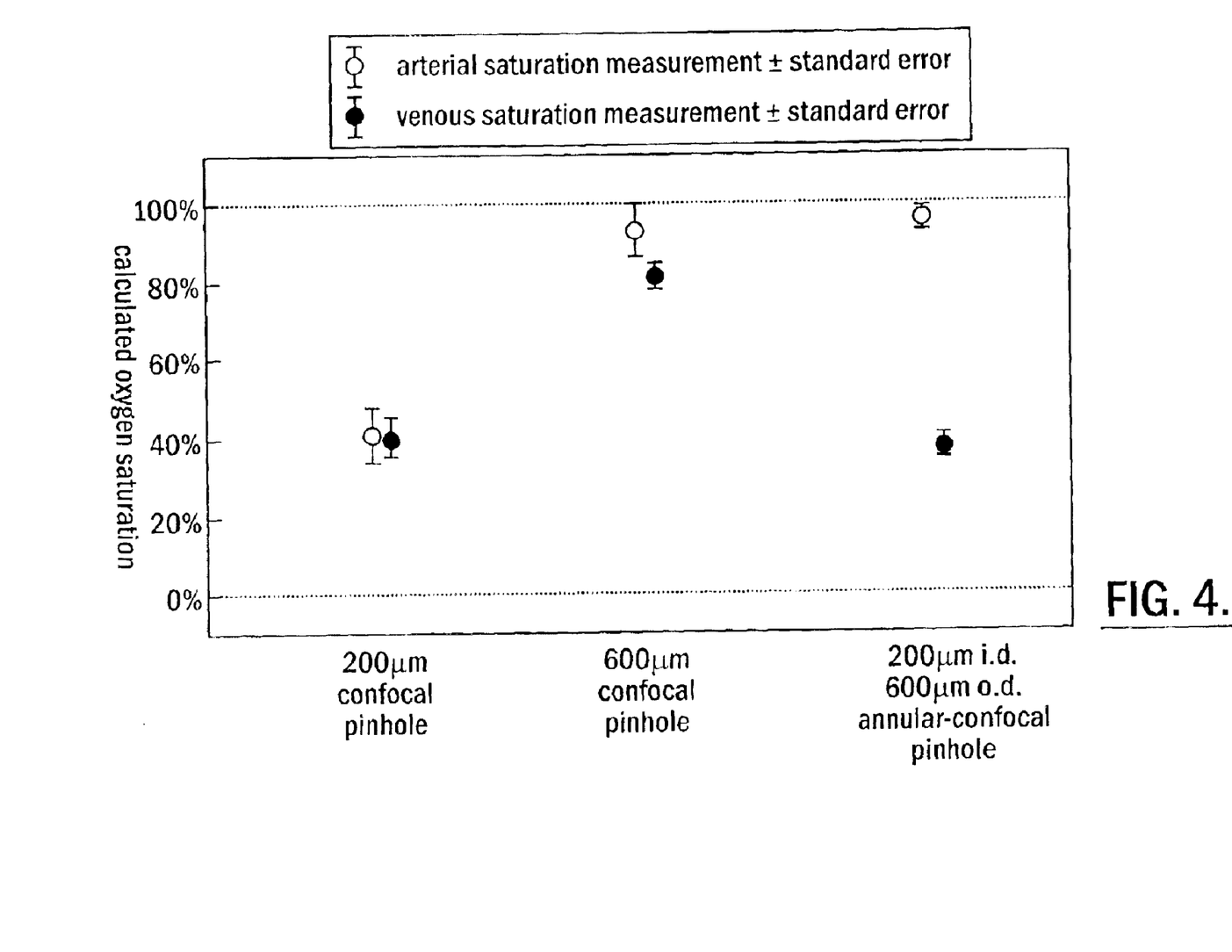
FIG. 4 is a graph depicting arterial and venous saturation measurements obtained by the method and apparatus of one embodiment of the present invention in comparison to measurements obtained by the use of two different confocal pinhole apertures.

In this regard, the apparatus and method of the present invention are capable of accurately determining both the relatively high blood oxygen saturation values for a retinal artery and the much lower blood oxygen saturation values for a retinal vein. For example, arterial saturation measurements are normally anticipated to be about 96% and venous saturation measurements are normally anticipated to be between about 40% and 60%. As depicted in FIG. 4, the method and apparatus of one embodiment of the present invention that only analyzes the single pass optical signals and that blocks the other optical signals can determine the widely separated arterial and venous saturation measurements. In this embodiment, the apparatus 10 includes an aperture having an annulus configuration with the annular transmissive portion 32 having an inner diameter of 200 micrometers and an outer diameter of 600 micrometers. With respect to FIG. 4, it is noted that the arterial and venous saturation measurements are represented by open and filled circles, respectively, with the standard error of the mean being represented by a vertical line extending upwardly and downwardly from the circle.

By way of comparison, the same retinal artery and vein were examined by an apparatus that did not include the annular aperture, but instead included an aperture that merely defined a pinhole at the focal point of the optical signals, i.e., a confocal pinhole. The aperture of this other apparatus was disposed between the focusing lens and the detector such that only those optical signals on axis that are focused to the pinhole are passed through the pinhole for collection by the detector. For a pinhole having a 200 micrometer diameter, the arterial and venous saturation measurements are approximately the same with both being between about 40% and 50%. As such, this relatively small pinhole renders the system insensitive to changes in oxygen saturation. In contrast, for a pinhole having a 600 micrometer diameter, the arterial and venous saturation measurements are both above 80% and are separated by only slightly more than the standard error of the mean. As such, in these instances, retinal arteries and veins are barely distinguishable.

In contrast, the method and apparatus 10 of the present invention can accurately determine the oxygen saturation of blood within a retinal vessel. Accordingly, the various applications that rely upon oxygen saturation measurements will receive higher quality data.

Figure 5:
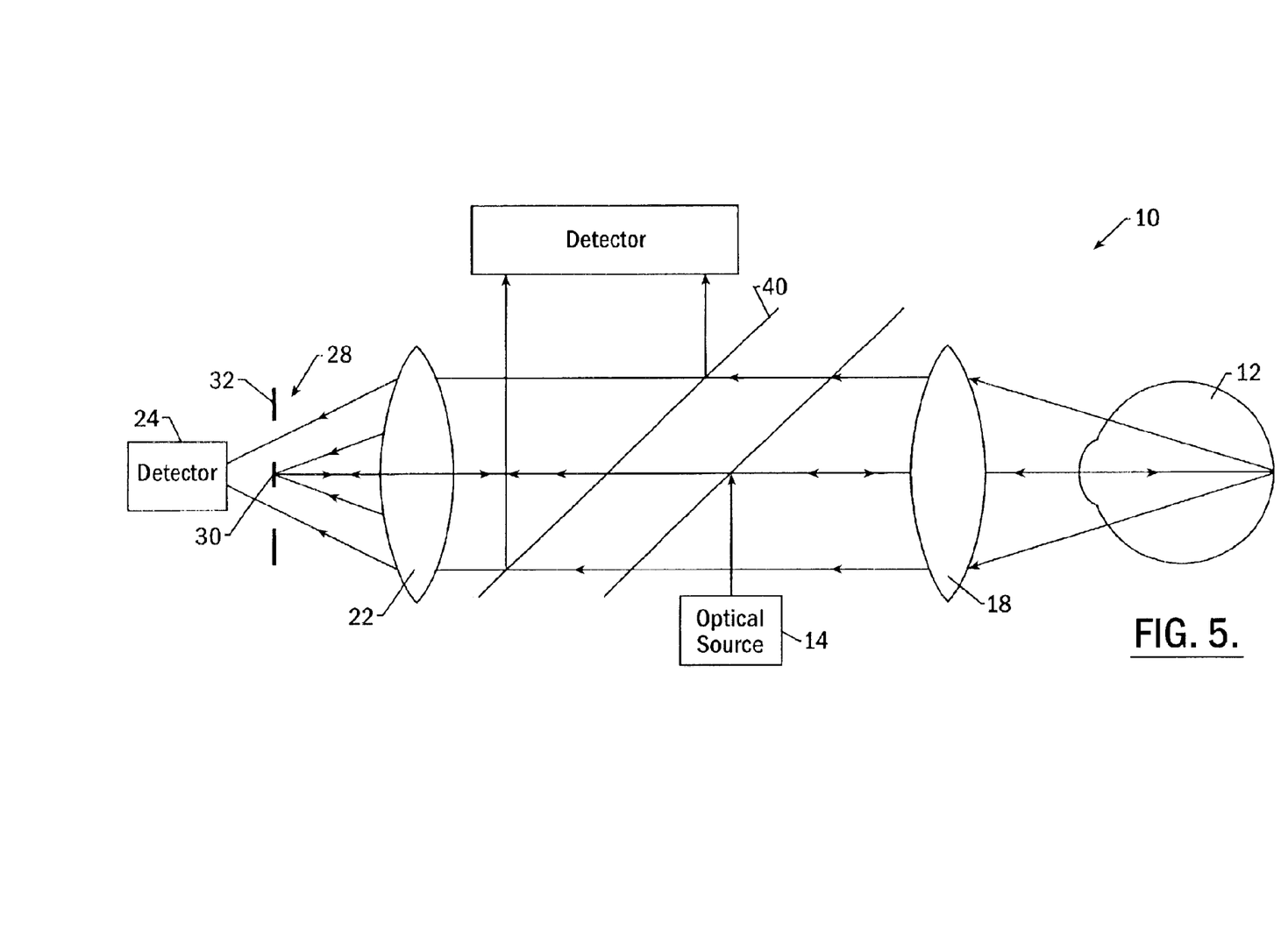
FIG. 5 is a block diagram of an apparatus for measuring the blood oxygen saturation in a retinal vessel according to another embodiment of the present invention.

As described above, the other optical signals that have been separated from the single pass optical signals may be blocked by the filter 28 with the filter absorbing or diffusing these other optical signals, for example. Alternatively, the filter may reflect or redirect the other optical signals as shown in the embodiment depicted in FIG. 5. In embodiments in which an aperture serves as the filter, the central spot 30 of the aperture may be reflective, such as by being formed of or coated with silver, aluminum, chromium or another reflective material. As such, the other optical signals that impinge upon the central spot will be appropriately redirected, such as to a beam splitter 40 which further redirects the other optical signals as shown in FIG. 5. In one embodiment, the other optical signals that are redirected are also measured or detected, albeit separately from the single pass optical signals by a second detector or the like. By also detecting the other optical signals, the processing element 36 can construct images of the retinal vessel based upon both the single pass optical signals and the other optical signals. As a result, the images constructed by the processing element of this embodiment will generally have a higher contrast relative to the images constructed by processing element based solely upon the single pass optical signals as shown in FIG. 3.

In addition to or instead of utilizing the other optical signals in the construction of images of the retinal vessel, the other optical signals that have been redirected by the filter 28 may be measured by the detector 24 and utilized by the processing element 36 to further determine the blood oxygen saturation. In this instance, the processing element could determine the blood oxygen saturation based upon the same equations as set forth above, although $\chi$ would no longer be 1 as in instances in which only single pass optical signals are detected and analyzed. Instead, $\chi$ would be 2 if only these other optical signals were utilized to determine the blood oxygen saturation. Or, more likely, if both the single and double pass optical signals were separately detected and utilized to determine the blood oxygen saturation the processing element would utilize an equation for transmittance having two terms of the type set forth by equation (3) with one term associated with the single pass optical signals and having $\chi$ set equal to 1 and the other term associated with the double pass optical signals and having $\chi$ set equal to 2. While an analysis based upon both the single pass optical signals and the other optical signals utilizes more complex equations than those utilized in embodiments in which only single pass optical light is analyzed, this analysis may provide greater accuracy in data reduction. As will be apparent to those skilled in the art, the processing element may similarly utilize an equation for transmittance having additional terms (in addition to those for single and double pass optical signals) for the contributions of optical signals that reflected from the retinal vessel and/or that were backscattered from red blood cells within the retinal vessel. However, these additional terms are typically quite small and can be treated as negligible for purposes of simplifying the analysis.

As described above, the filter 28 can be binary in nature in that it passes all of the off-axis signals, i.e., the single pass optical signals, and blocks all of the on-axis signals, i.e., the other optical signals that have been separated from the single pass optical signals. The filter may be graded in transmissivity, however, so as to pass different percentages of the incident optical signals, including both single pass optical signals and other optical signals, if so desired. In this regard, the filter may be graded in transmissivity from one region that rejects a greater percentage of the incident optical signals to another region that rejects a lesser percentage of the incident optical signals. The filter may be graded in various manners, but, in embodiment, is graded in a radial direction with the percentage of the incident optical signals that are rejected decreasing in radial direction extending from a center of the filter to the periphery of the filter. As will be apparent, the optical signals detected will therefore include both single pass optical signals and the other optical signals with the optical signals that are incident upon a central region of the filter including a greater percentage of the other optical signals and the optical signals that are incident upon an outer region of the filter including a greater percentage of the single pass optical signals. As such, the processing element will utilize a value of $\chi$ between 1 and 2 in order to determine the blood oxygen saturation, with the value of $\chi$ depending upon the relative percentages of the single pass optical signals and the other optical signals that are transmitted by the filter on an overall basis. By properly designing the graded filter, the method and apparatus of this embodiment of the present invention can be tailored in accordance with a particular situation.

The filter 28 of this embodiment may be graded in various manners. In one embodiment in which the filter is coated with a metal, such as silver, aluminum, chromium or the like, and is at least partially reflective, the gradation in the transmissivity of the filter may be accomplished by controlling the thickness of the metallic coating. In this regard, thicker coatings are generally more reflective and thinner coatings are generally more transmissive. In the embodiment in which the filter is radially graded such that medial portions of the filter reflect a greater percentage of the optical signals than peripheral portions of the filter, the thickness of the metallic coating may decrease in a radial direction from the center of the filter which has a relatively thick metallic coating to peripheral portions of the filter which have a relatively thin metallic coating.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. An apparatus for separately detecting single pass optical signals that return from an eye in order to measure blood oxygen saturation in a retinal vessel, the apparatus comprising:
    an optical source for illuminating a retinal vessel within the eye with optical signals;
    a filter disposed within the path of the optical signals returning from the eye, said filter capable of separating single pass optical signals that return from the eye after only traversing the retinal vessel once from other optical signals that return from the eye, wherein said filter is disposed within a focal plane of the optical signals returning from the eye; and
    a detector for detecting at least the single pass optical signals that have been separated by said filter; and
    a processing element for determining the blood oxygen saturation within the retinal vessel based at least partially upon the single pass optical signals detected by said detector.

2. An apparatus according to claim 1 wherein said filter comprises an aperture having a central stop and a transmissive portion at least partially surrounding the stop to preferentially pass the single pass optical signals.

3. An apparatus according to claim 2 wherein said aperture is selected from the group consisting of an annulus, an anti-pinhole, a slit-annulus and an anti-slit.

4. An apparatus according to claim 1 wherein said filter is graded from one region that rejects a greater percentage of incident signals to another region that rejects a lesser percentage of the incident optical signals.

5. An apparatus according to claim 1 wherein said detector separately detects the other optical signals that have been separated from the single pass optical signals by said filter.

6. An apparatus according to claim 5 wherein said filter comprises an aperture having a central stop and a transmissive portion at least partially surrounding the stop to preferentially pass the single pass optical signals, wherein the central stop is at least partially reflective to reflect the other optical signals that have been separated from the single pass optical signals.

7. An apparatus for measuring blood oxygen saturation in a retinal vessel within an eye, the apparatus comprising:
    a filter disposed within the path of optical signals returning from the eye, said filter capable of separating single pass optical signals that return from the eye after only traversing the retinal vessel once from other optical signals that return from the eye, wherein said filter comprises an aperture having a central stop and a transmissive portion at least partially surrounding the stop to preferentially pass the single pass optical signals;
    a detector for detecting at least the single pass optical signals that have been separated by said filter; and
    a processing element for determining the blood oxygen saturation within the retinal vessel based at least partially upon the single pass optical signals detected by said detector.

8. An apparatus according to claim 7 said filter is disposed within a focal plane of the optical signals returning from the eye.

9. An apparatus according to claim 7 wherein said aperture is selected from the group consisting of an annulus, an anti-pinhole, a slit-annulus and an anti-slit.

10. An apparatus according to claim 7 wherein said filter is graded from one region that rejects a greater percentage of incident optical signals to another region that rejects a lesser percentage of the incident optical signals.

11. An apparatus for measuring blood oxygen saturation in a retinal vessel within an eye, the apparatus comprising:
    a filter disposed within the path of optical signals returning from the eye, said filter capable of separating single pass optical signals that return from the eye after only traversing the retinal vessel once from other optical signals that return from the eye;
    a detector for detecting at least the single pass optical signals that have been separated by said filter, wherein said detector separately detects the other optical signals that have been separated from the single pass optical signals by said filter; and
    a processing element for determining the blood oxygen saturation within the retinal vessel based at least partially upon the single pass optical signals detected by said detector.

12. An apparatus according to claim 11 wherein said filter comprises an aperture having a central stop and a transmissive portion at least partially surrounding the stop to preferentially pass the single pass optical signals, wherein the central stop is at least partially reflective to redirect the other optical signals that have been separated from the single pass optical signals.

13. An apparatus according to claim 11 wherein said processing element also determines the blood oxygen saturation within the retinal vessel based at least partially upon the other optical signals that are separately detected by said detector.

14. A method for measuring blood oxygen saturation in a retinal vessel within an eye, the method comprising:
    separating single pass optical signals that return from the eye after only traversing the retinal vessel once from other optical signals that return from the eye;
    detecting at least the single pass optical signals that have been separated from the other optical signals; and
    determining the blood oxygen saturation within the retinal vessel based at least partially upon the single pass optical signals that have been detected.

15. A method according to claim 14 wherein separating the single pass optical signals from the other optical signals comprises blocking the optical signals returning from the eye that are focused upon a stop while passing optical signals that are offset from the stop.

16. A method according to claim 14 wherein separating the single pass optical signals from the other optical signals comprises redirecting the other optical signals that are returning from the eye.

17. A method according to claim 14 wherein detecting at least the single pass optical signals comprises separately detecting the other optical signals that have been separated from the single pass optical signals.

18. A method according to claim 14 wherein determining the blood oxygen saturation within the retinal vessel comprises determining the blood oxygen saturation within the retinal vessel based upon both the single pass optical signals and the other optical signals that have been separately detected.

* * * * *